United States Patent
Mash et al.

(10) Patent No.: US 11,207,429 B2
(45) Date of Patent: *Dec. 28, 2021

(54) METHOD AND COMPOSITIONS FOR ORALLY ADMINISTERED CONTRAST AGENTS FOR MR IMAGING

(71) Applicants: THE ARIZONA BOARD OF REGENTS ON BEHALF OF THE UNIVERSITY OF ARIZONA, Tucson, AZ (US); H. Lee Moffitt Cancer Center and Research Institute, Tampa, FL (US)

(72) Inventors: Eugene A. Mash, Tucson, AZ (US); Parastou Foroutan, Tampa, FL (US); Suryakiran Navath, Tucson, AZ (US); Robert J. Gillies, Tampa, FL (US); Gary V. Martinez, Tampa, FL (US); David L. Morse, Tampa, FL (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/316,810

(22) PCT Filed: May 11, 2015

(86) PCT No.: PCT/US2015/030200
§ 371 (c)(1),
(2) Date: Dec. 6, 2016

(87) PCT Pub. No.: WO2015/172155
PCT Pub. Date: Nov. 12, 2015

(65) Prior Publication Data
US 2017/0209602 A1    Jul. 27, 2017

Related U.S. Application Data

(60) Provisional application No. 61/991,236, filed on May 9, 2014.

(51) Int. Cl.
A61K 49/10 (2006.01)
A61K 49/12 (2006.01)
A61K 49/08 (2006.01)

(52) U.S. Cl.
CPC .......... *A61K 49/108* (2013.01); *A61K 49/085* (2013.01); *A61K 49/124* (2013.01)

(58) Field of Classification Search
CPC ....... A61K 49/08; A61K 49/108; A61K 47/48
See application file for complete search history.

(56) References Cited

U.S. PATENT DOCUMENTS

| | | | |
|---|---|---|---|
| 2005/0048000 A1* | 3/2005 | Gervais | A61K 51/0497 424/9.364 |
| 2014/0105827 A1* | 4/2014 | Morse | C12Q 1/6886 424/9.34 |
| 2014/0228551 A1* | 8/2014 | Tworowska | C07H 17/07 534/10 |

OTHER PUBLICATIONS

Daniel J. Mastarone et al., A Molecular System for the Synthesis of Multiplexed Magnetic Resonance Probes, JACS, 133, 5329-5337. (Year: 2011).*
Gary V. Martinez et al., Demonstration of a Sucrose-derived Contrast Agent for Magnetic Resonance Imaging of the GI Tract, Biorg Med Chem Lett, 23(7), 2061-2064. (Year: 2013).*
Venkataramana Rao et al. A Sucrose-derived Scaffold for Multimerization of Bioactive Peptides, Bioorg Med Chem, 19(21), 6474-6482. (Year: 2011).*

* cited by examiner

*Primary Examiner* — Johann R Richter
*Assistant Examiner* — Jagadishwar R Samala
(74) *Attorney, Agent, or Firm* — Don D. Cha; HDC Intellectual Property Law, LLP

(57) ABSTRACT

Disclosed is CT or MR contrast agent which comprises a base or carrier scaffold formed of a polyhydroxol compound having a linker to which a Gd-DOTA is covalently bonded. Also disclosed is a method of screening a patient for colon cancer using a CT or MR contrast, which method comprises administering to a patient undergoing screening a compound as above described.

8 Claims, 5 Drawing Sheets

Elemental Analysis

| Mouse # | Gadolinium (wt%) | | |
| --- | --- | --- | --- |
| | Colon | Urine | Feces |
| 1 | < 10 ppm | < 5 ppm | 127 ppm (± 8.47) |
| 2 | < 12 ppm | < 20 ppm | 128 ppm (± 4.52) |
| 3 | < 12 ppm | < 10 ppm | 126 ppm (± 4.23) |
| 4 | < 11 ppm | < 10 ppm | 125 ppm (± 3.02) |

Fig. 5

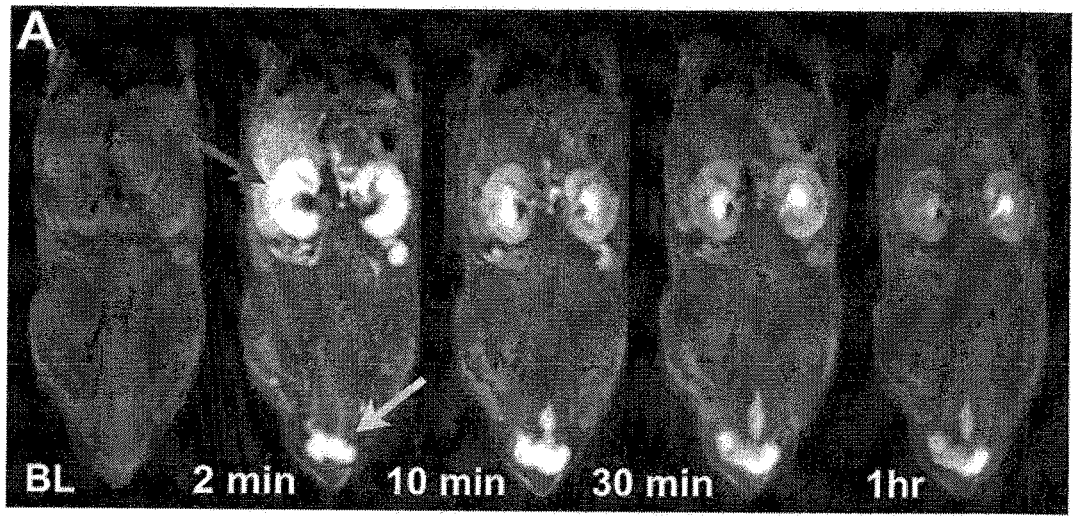
Fig. 6A
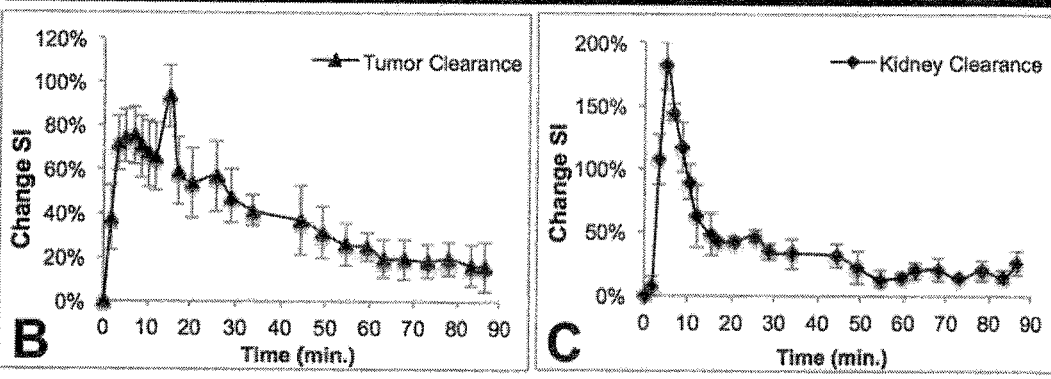
Fig. 6B
Fig. 6C

METHOD AND COMPOSITIONS FOR ORALLY ADMINISTERED CONTRAST AGENTS FOR MR IMAGING

CROSS-REFERENCE TO RELATED APPLICATIONS

This application is a U.S. National Stage Patent Application of PCT Patent Application No. PCT/US2015/030200, filed May 11, 2015, which claims the priority benefit of U.S. Provisional Application Ser. No. 61/991,236, filed May 9, 2014, the contents of which are incorporated herein by reference.

STATEMENT REGARDING FEDERALLY FUNDED RESEARCH

This invention was made with government support under Grant Nos. R01 CA097360, R01 CA123547, R33 CA095944, and P30 CA023074 awarded by the National Institutes of Health. The government has certain rights in the invention.

BACKGROUND OF THE INVENTION

This invention relates generally to the field of medicine, and more specifically to protection and diagnosis of dysplastic and early neoplastic colonic lesions. More specifically, the disclosure relates to targeted molecular imaging agents for early detection of colon cancer via colonography using CT or MR contrasts and to methods for using such imaging agents, and will be described in connection with such utility, although other utilities are contemplated.

Colorectal cancer (CRC) is the third most common cancer in both males and females, and the second leading cause of death from cancer in the United States (1). Each year, over 140,000 new cases of CRC, mainly affecting adults 50 years of age and older, are diagnosed in the US alone, and the expected deaths exceed 50,000 (2, 3). Similar to other cancers, the choice of treatment for CRC depends mainly on disease stage and physical state of the patient, but most often includes surgical resection followed by chemo- and radiation therapy. During the past decades, much progress has been made in understanding the biological underpinnings of CRC and developing novel targeted chemotherapeutic agents. However, the prognosis still relies heavily on early-stage-disease detection, thus emphasizing the need for an efficient screening method.

Various screening methods for CRC, including fecal occult blood testing, flexible sigmoidoscopy and air-contrast barium enema examination have been available for decades, but, poor sensitivity and limited spatial coverage have often yielded false-positive results (4). As a consequence of these inaccurate results, further unnecessary tests have been carried out using the current standard of care for CRC screening, colonoscopy. Colonoscopy is highly invasive, requires intravenous sedation, and a pre-operative intake of large volumes of purgatory liquids. In addition, colonoscopy has been found to miss smaller (<7 mm) and/or flat-shaped polyps (5, 6). Due to aforementioned factors and severe discomfort, many eligible adults do not comply with physician recommendations and do not undergo the procedure.

To address issues with diagnostic inaccuracy, cost, and patient non-compliance, as a non-invasive alternative, cross-sectional imaging modalities such as computed tomographic colonography (CT-C) and magnetic resonance colonography (MR-C) have been employed for colon evaluations in recent years. Both modalities (summarized as "virtual colonoscopy") provide high spatial resolution three-dimensional (3D) datasets that encompass the entire colon, and have a higher patient acceptance than conventional colonoscopy (7). In comparison to colonoscopy, CT-C presents minimal physical risks, has a short procedure time (~10 min), and can be performed in patients with distal occluding lesions. On the downside, this technique still requires bowel cleansing, is rather costly, and more importantly, is as insensitive to small and flat polyps as standard colonoscopy (8-10). In addition, radiation is a serious concern and impacts patient compliance significantly. Although MR-C also is a costly technique, the lack of ionizing radiation, anesthetics, and excellent soft-tissue contrast favors the use of MR as the modality of choice for detecting and monitoring colorectal polyps.

To date, most clinical and pre-clinical MR-C evaluations have employed bright-lumen contrast (11, 12). More recently, several animal studies have developed and applied the simplified technique of dark-lumen MR-C (13-15). Although dark lumen MR-C, which utilizes heavily $T_1$-weighted sequences and a contrast enhancing agent (i.e. Gd-DOTA or Gd-DTPA), has shown a better performance than the bright-lumen approach, an enema or bowel distension is still needed. To increase the sensitivity of MR-C, Gd-based contrast agents (e.g. Magnevist) are commonly used via intravenous delivery. However, these agents are not specifically targeted to CRC. To overcome these drawbacks, an object of this disclosure is to develop an improved Gd-based targeted contrast agents for pre-screening of CRC by MRI, that can be administered orally, is non-toxic and can pass through the GI-tract without being degraded and/or absorbed. In addition, this contrast agent would be sensitive enough such that relatively low concentrations and volumes can be used to achieve a substantial signal enhancement and, thus, an enema would not be required.

SUMMARY OF THE INVENTION

Previously, we introduced the first generation of orally administered Gd-DOTA-Sucrose contrast agents for three-dimensional MR imaging of the mouse gastro-intestinal (GI) tract (16). We showed that our contrast agent had superior relaxometric properties compared to Gd-DOTA in its lower limit of detectability, remained in the GI tract throughout its passage, and potentially could be targeted to colon lesions using in-house developed high-affinity marker-specific binding ligands.

The present disclosure provides improvements over our earlier Gd-DOTA-Sucrose contrast agents by increasing the average number of Gd-DOTA chelates per sucrose molecule to 8. More importantly, in order to improve the relaxivity (17), the length of the linkers joining the chelates to the sucrose scaffold was shortened to yield a less conformationally mobile compound, thus increasing the rotational correlation time. Preferably the linker comprises a straight chain or branched segment composed of a hydrocarbon, preferably containing four carbon atoms.

In one aspect of the disclosure there is provided a CT or MR contrast agent comprising a base or carrier scaffold formed of a polyhydroxol compound having a linker to which a Gd-DOTA is covalently bonded.

For a preferred embodiment of the disclosure the polyhydroxol compound comprises a monosaccharide.

In a particularly preferred embodiment of the disclosure the polyhydroxol compound comprises sucrose.

In a further and even more preferred embodiment of the disclosure, the polyhydroxol compound comprises sucrose, and the number of Gd-DOTA chelates bonded to the sucrose is 8.

In one embodiment of the disclosure the linker incorporates one or more straight chain hydrocarbon segments.

In another embodiment of the disclosure the linker incorporates one or more branch chain hydrocarbon segments.

The present disclosure also provides a method of screening a patient for colon cancer using a CT or MR contrast, which method comprises administering to a patient undergoing screening the above-described compound.

The present disclosure also provides a method for screening a patient for colon cancer using a CT or MR contrast wherein CRC cells are screened for.

Using MR imaging at 7 T, initial relaxation experiments were performed with phantoms containing the agent in different concentrations. A progressive saturation pulse sequence was employed and a linear regression model used for quantification of the molar relaxivity. In vivo, the agent was administered by both oral gavage and intravenous injection in mice bearing orthotopic CRC xenograft tumors and evaluated by coronal $T_1$-weighted spin-echo multislice (SEMS) imaging both prior to, and post, contrast. The ramifications of these findings and plans for future development are discussed within this manuscript.

Further features and advantages of the present disclosure may be seen in the following detailed description, taken in conjunction with the accompanying drawings.

BRIEF DESCRIPTION OF THE DRAWINGS

FIG. 5 is a table of elemental analysis of Gadolinium levels in the colon and the urine;

FIG. 6A shows $T_1$ weighted Spin Echo Multi Slice images at various times post IV injection of contrast agent of the present disclosure; and FIGS. 6B and 6C are graphs plotting quantitative data showing signal intensity with time in the tumor (FIG. 6B) and the kidneys (FIG. 6C).

DETAILED DESCRIPTION OF THE INVENTION

Contrast Agent

Figure 1:
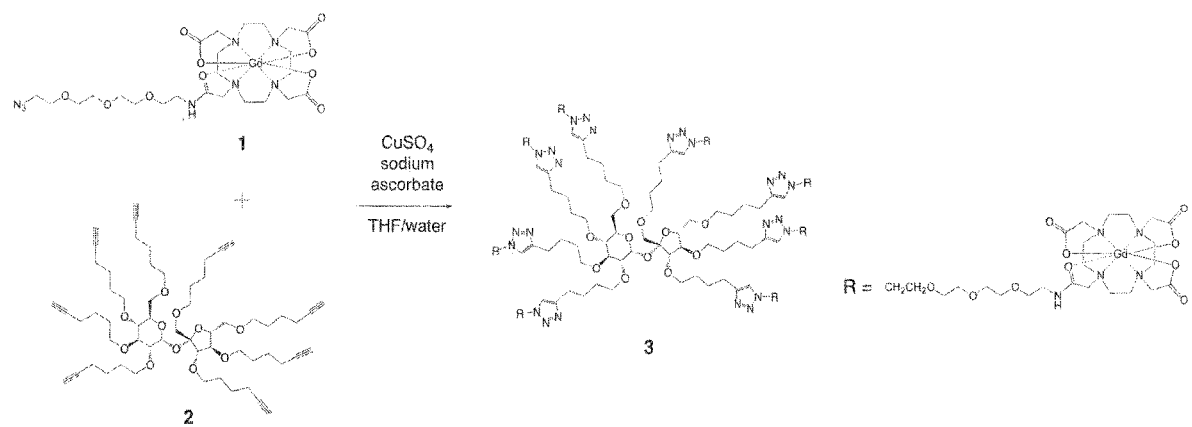
FIG. 1 illustrates a reaction scheme for synthesizing a contrast agent in accordance with one embodiment of the disclosure.
Figure 2:
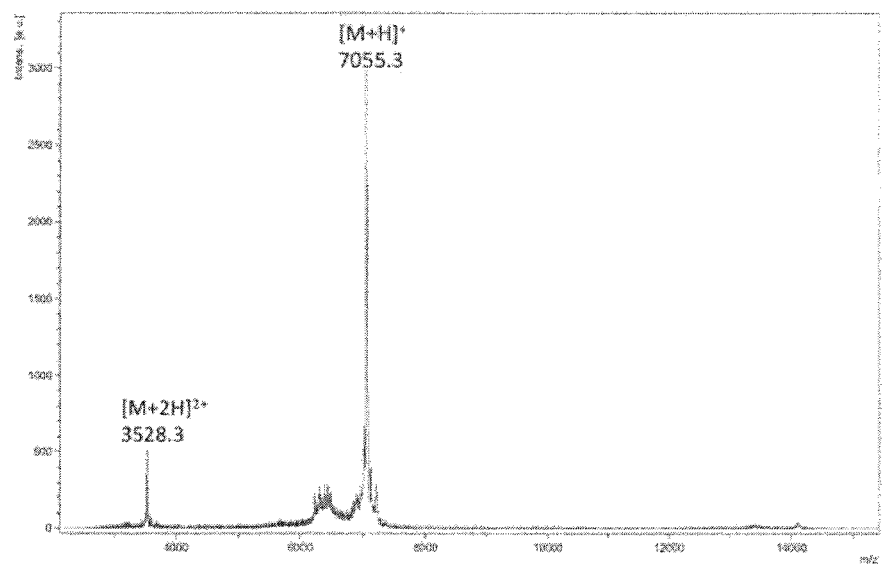
FIG. 2 is a mass spectrometric analysis of the contrast of the agent synthesized in accordance with FIG. 1.

The synthesis of the sucrose-derived contrast agent 3 is depicted in FIG. 1. To an argon-degassed solution of azide 1 (16) (1.85 g, 2.43 mmol) and octaalkyne 2 (18) (271 mg, 0.28 mmol) in 9/1 THF/water (50 mL) were added $CuSO_4$ (80 mg, 0.5 mmol) and sodium ascorbate (160 mg, 0.8 mmol). The mixture was stirred under argon at room temperature for 24 h. Volatiles were evaporated and the residue was diluted with water (50 mL), the solution was washed with a mixture of dithiazone in chloroform (20 mg/L, 5×100 mL), and lyophilized to give a residue, which was loaded onto a reversed phase (C-18) silica gel column. The column was eluted with acetonitrile/water (80/20) to yield the product 3 as a non-hygroscopic cream-colored solid (1.81 g, 0.25 mmol, 89%). MALDI-TOF MS was performed as shown in FIG. 2, and calculated for $C_{252}H_{414}N_{64}O_{91}Gd_8$ was 7056.366 $[M+H]^+$, while we observed at 7056.328, and at $3528[M+2H]^{2+}$ confirming the presence of 8 Gd-DOTA chelates per sucrose scaffold.

Phantom Evaluations

Initial MRI characterization of the Gd-DOTA-Sucrose compound was accomplished in phantoms of varying concentrations according to previously described protocol (16). Similarly, these phantoms were studied using progressive saturation experiments (PS), with 11 TR values exponentially spaced from 30 s to 60 ms. Nonlinear least squares regression was employed to determine the relaxation time- and relaxation rate constants, $T_1$ and $R_1=1/T_1$, respectively. Weighted linear regression was used to determine the $R_1$ value as a function of concentration, and the relationship between $R_1$ and [Gd-DOTA-sucrose CA] was estimated for the average multimer. The weights used in the fit were inversely proportional to the variance in $R_1$ for each concentration, $(1/s^2_{R1,i})$.

EXAMPLES

In vivo Experiments

A human colorectal cell line engineered to express luciferase (HCT-116/Luc) was used to generate orthotopic CRC xenograft tumors. Eight female SCID/beige mice each received injections into the lining of the rectum, 4-5 mm beyond the anal verge, of $1\times10^6$ HCT 116/luc cells in a 10 μl volume (mixed in a solution of X uL PBS). Mice were allowed to recuperate for two weeks, while being weighed daily, and then monitored for tumor growth by bioluminescence imaging in the IV IS 200 (Perkin Elmer) 2 times per week. After approximately 2 weeks, tumor growth also was monitored via $T_2$-weighted MRI (spin echo multi slice sequences with TE/TR=72/1000 ms, slice thickness of 0.785 mm and resolution of 350×350×100 um over 6 minutes). Upon tumor detection (~3 weeks after injection), contrast enhanced imaging experiments were initiated.

Compound 3 was dissolved in 100 mM sodium phosphate buffer, pH 7.4, at a concentration of 2.5 mM for gavage administration. Gavage was given at 10 μl per gram of body weight. Imaging began within 30 minutes of contrast agent administration. For i.v. contrast administration, compound 3 was dissolved in PBS at a concentration of 25 μmol/kg of body weight, and administered in 150 μl volume via tail vein catheter during the imaging session, with image acquisition occurring before, during and after injection.

Imaging Protocol & Analysis

MRI was performed at baseline and at 30 minutes and at 5, 24 and 48 hours following gavage administration. All imaging data were acquired using a 7-T horizontal magnet (ASR 310, Agilent Technologies) equipped with nested 305/120/HDS gradient set. Prior to acquisitions, animals were placed in an induction chamber and anesthetized using 2% isoflurane. The mice were then restrained in a specific holder and inserted into the magnet and 35-mm quadrature coil (Doty Scientific) with a constant supply of isoflurane and heated air gas in order to maintain a temperature of 37±1° C. Body temperature and respiratory functions were monitored using the SAII system (Small Animals Instrument Inc, Stony Brook, N.Y.) and temperature control of the imaging gradients was achieved by means of a water chiller (Neslab Waters) and maintained at 12° C. for all acquisitions. Applying a coronal slice orientation, 3-dimensional $T_1$-weighted spin-echo (SE3D) sequences were acquired with TE/TR=10.6/31.6 ms, field of view=90×45×16 mm, matrix=256×128×16 and four averages in 4.3 min. Images were acquired prior to contrast and at 30 min, 5, 25 and 48 hours post gavage.

For the dynamic scans, contrast was administered via tail vein catheter during imaging with two dimensional spin-echo multislice (SEMS) with $T_1$-weighting using TE/TR=10/233 ms, field of view=90×45 mm, matrix=256×128 and 9 slices with 1 mm thickness. The total scan time equaled 90 min (5 min prior to contrast and 85 min post). For both scans, spatial resolution was hence 351×351×1000 µm.

Signal intensity (SI) in the tumors and kidneys was calculated using manually drawn regions of interest (ROIs) in VnmrJ (Agilent Technologies, Inc.) and normalized to surrounding tissue intensity. Each mouse was used as its own control and the percent increase in SI was calculated individually and then averaged.

Statistical analysis was performed using Graphpad Prism software (Graphpad, San Diego, Calif., USA) and one-way analysis of variance (ANOVA) followed by the Tukey test for comparison of mean values. A confidence interval of 95% was chosen and thus statistical significance was predetermined at p<0.05.

Elemental Analysis

For elemental analysis studies, four female SCID mice weighing between 24 and 26 grams each were administered 200 µl of compound 3 in 0.1 M sodium phosphate buffer via oral gavage. This delivers 3.52 mg of 3 (GdSucrose) into each mouse. Mice were then immediately transferred individually to metabolic caging, designed to separately capture urine and feces. After 72 hours, mice were euthanized and colons were removed, lightly rinsed with PBS and collected in individual tubes. Urine and feces were collected separately. All samples were lyophilized, and subsequently sent to Elemental Analysis, Inc., (Lexington, Ky.) for detection of gadolinium via instrumental neutron activation analysis (INAA).

Histology

Following MRI, animals were euthanized and tumor sections fixed, mounted in paraffin, cut into sections, mounted on slides and stained with Hematoxylin & Eosin (H & E) for histology examination.

Results

The calculated mass for compound 3 ($C_{252}H_{414}N_{64}O_{91}Gd_8$) is 7056.366 [M+H]$_+$. By MALDI-TOF MS (FIG. 2), the observed mass was 7056.328, and the average number of Gd-DOTA chelates per sucrose was determined to be 8. During the phantom portion of this study, it was noted that the solubility of this current compound 3 differed substantially from the CA previously presented by Martinez et al (19). Specifically, we observed that while 3 dissolved rather easily in water or aqueous buffer, the previous compound was not soluble in water and required 15% ethanol to achieve suspension.

Figure 3A:
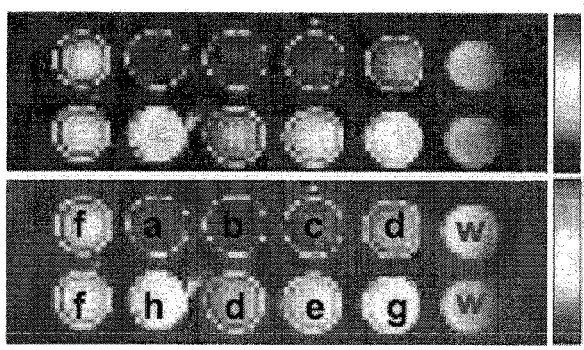
FIG. 3A are shaded $T_1$ maps demonstrating variance in $T_1$ times between phantoms of various concentrations.
Figure 3B:
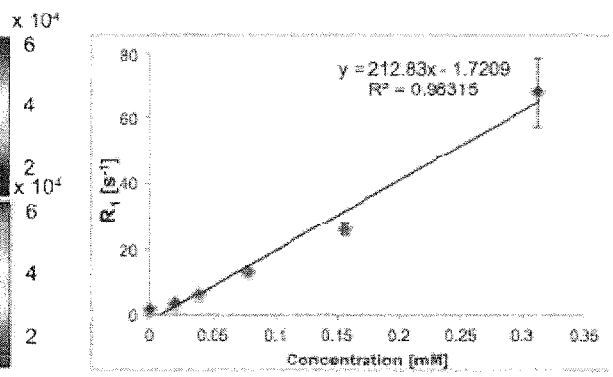
FIG. 3B is a graph showing weighted linear regression of experimental phantom data ($R_1$ as a function of concentration)

MR relaxivity measurements clearly demonstrated differences in $T_1$-shortening and thus contrast enhancement in the various phantoms (i.e. concentrations) could readily be observed in shaded $T_1$ maps (FIG. 3A). The shaded $T_1$ maps demonstrate the variance in $T_1$-times between phantoms of various concentrations. Phantom concentrations range as following [µM]; a=2500; b=1250; c=625; d=313; e=156; f=78; g=39; h=20 and w=0 (i.e. pure water). Note that a, b and c had to be excluded due to oversaturation effects. Due to shortening of spin-spin ($T_2$) relaxation, three of the highest concentration phantoms were excluded for quantitative analysis of relaxivity. To determine the molar relaxivity ($r_1$) of this improved agent, 3, a weighted linear regression model was applied to the phantom data (FIG. 3B). Impressively, the fitted value for molar relaxivity ($R_1$) was 213±1.7 mM s$^{-1}$ with $R^2$=0.983, which is an 8-fold increase compared to our previous compound (16). Relaxation experiments were accomplished with multiple TR spin echo experiments on two separate Eppendorf tube phantoms prepared with identical concentrations of Gd-DOTA-sucrose CA. Error bars denote standard deviations.

Figure 4A:
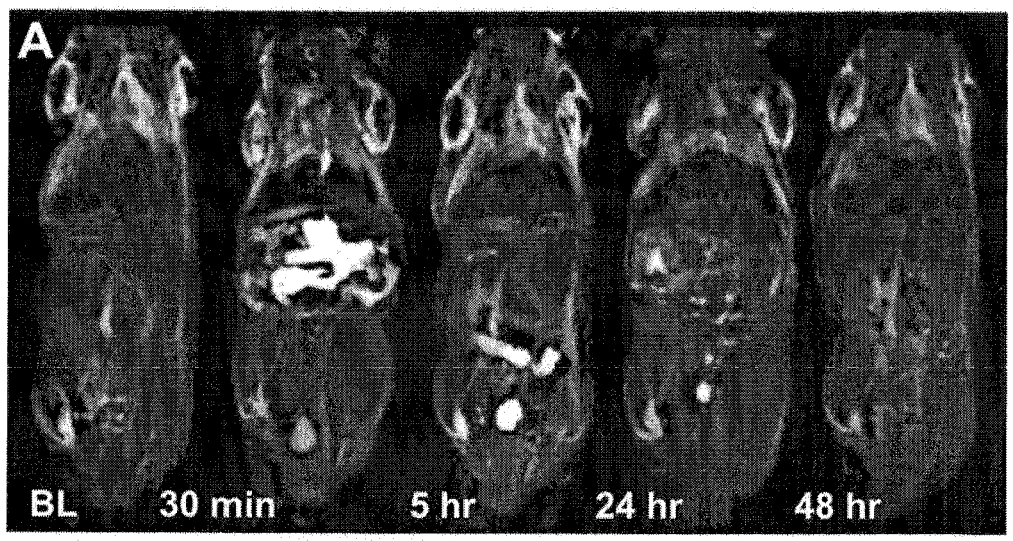
FIGS. 4A-4E are maximum intensity projections and relative contrast images demonstrating passage of the contrast agent of the present disclosure.

In vivo, the passage of the CA and potential tumor uptake in CRC xenografts were monitored by a series of two- and three-dimensional $T_1$-weighted sequences (see protocol). Herein clearly visualized by maximum intensity projections (MIP), the agent showed rather fast movement throughout the mouse GI-tract (FIG. 4A). Maximum Intensity Projections (MIP) generated from $T_1$-weighted Spin Echo sequences (3D) demonstrate the passage of CA throughout the gastrointestinal tract of a representative animal at baseline (BL) and 30 minutes at 5, 25 and 48 hours post gavage. In fact, as early as 30 min following gavage administration, the agent had moved from the stomach to the upper intestinal areas. At the 5-hour time point it appeared that the agent had partially cleared the animal with notable enhancement remaining in the intestines. By 24 hours, only small amounts of compound could be detected in the intestines and this contrast appeared to be associated with feces. By 48 hours post CA, we could no longer detect any enhancement.

Figure 4B:
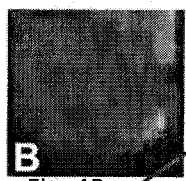
Figure 4C:
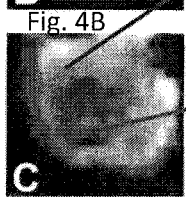
Figure 4D:
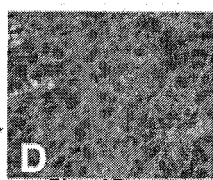
Figure 4E:
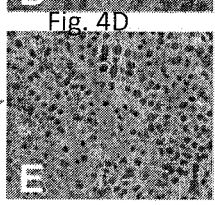

More importantly, and although non-targeted at this point, the contrast agent of the present disclosure induced notable signal enhancement in the tumors at 5 hours post-gavage. Zoomed in on the tumor solely, 3D Spin Echo images of pre-contrast FIG. 4B, and 5 hours post-gavage FIG. 4C, show the relative contrast enhancement. This enhancement was particularly noticeable in the tumor rim, and revealed a potentially necrotic core. To investigate this darker inner core further, H & E stained tumor sections were evaluated, and did indeed demonstrate substantial cellular necrosis in the tumor center versus the outer rim (FIGS. 4D & 4E). Additionally, enhancement was observed in the bladder at the 5 hour time-point, which was co-incident with tumor enhancement. Since we had previously not observed uptake of the original compound in the bladder (19), and the original study did not include tumors, while not wishing to be bound by theory, we believe that this could be due to systemic uptake through the orthotopic xenograft tumor.

Figure 4F:
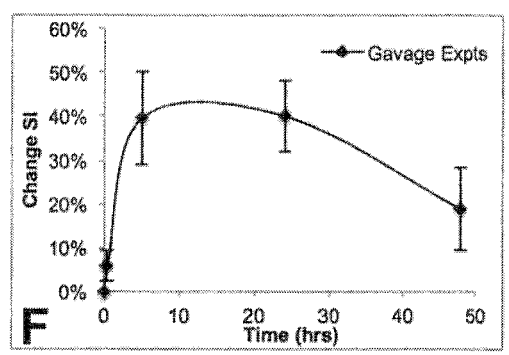
FIG. 4F plots change in tumor signal intensity compared to baseline values before contrast.

Quantitatively, tumor signal intensity (SI) was determined for each animal using manually drawn ROIs and compared to pre-gavage values. Confirming the visual observations, a significant increase of 40% in tumor SI was noted by 5 h post gavage and persisted throughout the 24-hour time point. See FIG. 4F which shows percent change in tumor signal intensity compared to baseline values before contrast. By 48 hours post CA administration, the enhancement had dropped to 20% above baseline values and the CA appeared to largely have cleared the animal. This observation was further confirmed by elemental analysis, which showed that the Gadolinium levels in the colon and urine were below the limits of detection, while a notable portion was found in the feces (see FIG. 5). Since the elemental analysis study was conducted using animals that did not bear tumors, and Gd was not detected in the colon tissue or urine, this observation further supports the idea that the bladder uptake in the MM study was due to systemic uptake via the orthotopic tumor and not uptake through the unaffected GI tract.

To evaluate the properties of this agent following intravenous administration and determine kidney clearance rates, mice (N=4) received contrast (compound 3) by an i.v. tail vein catheter while inside the magnet. As demonstrated in FIG. 6A which shows $T_1$-weighted Spin Echo Multi Slice (SEMS) showing baseline (BL), and at 2 minutes, 10 minutes, 30 minutes, and 1 hour post IV injection of contrast agent, dramatic signal enhancement within the tumor could be detected immediately following the i.v. injection (lower arrow 10) and the kidneys showed maximum uptake at this point (upper arrow). These observations were in agreement with quantitative analysis showing an increase of signal intensity of tumor contrast by 72% within the first 5 minutes following injection (FIG. 6B). By 15 minutes post CA, the increase in signal intensity reached 93%, following which, the signal intensity appeared to decrease exponentially. By 90 min, the signal intensity had dropped back to 16% above baseline values and the imaging session was terminated. Kidney clearance of the CA was also quantified and showed an increase in signal intensity of 185% by 3 min post injection followed by a fast wash-out of the agent (FIG. 6C).

Neutron activation analysis specifically detected gadolinium in colon tissue, urine and feces collected over the first 72 hours post gavage. Detection of gadolinium in urine and colon tissue was under 5 ppm or less in all samples, which is the limit of detection of the analysis. In feces, the samples averaged 126.5 ppm. This indicates that most, if not all, of the Gd-DOTA-Sucrose probe passed through the GI tract and was excreted in the feces. These non-tumor bearing mice did not have measurable excretion through the urine or uptake in colon tissue, in contrast to what was seen in tumor-bearing mice during imaging sessions.

The present disclosure provides the following features and advantages:
- Our first generation Gd-DOTA-sucrose contrast agents had superior relaxometric properties compared to Gd-DOTA in its lower limit of detectability and remained in the GI tract throughout the passage.
- In this study, we improved our first generation Gd-DOTA-sucrose contrast agents by increasing the average number of Gd-DOTA chelates per sucrose to 8.
- To improve relaxivity, the chelates were shortened to induce stiffness thus increasing the rotational correlation time.
- These modifications yielded an 8-fold increase in Spin-Lattice-relaxivity which also was observed in vivo (212 from 29). The new molecule has shorter arms and limits motion and rapidly clears the kidney.
- In vivo, tumor signal intensity enhanced 40% (gavage) and 93% (tail-vein injection).
- Kidney uptake was maximized by 3 min post i.v. injection and cleared by 10 min (significantly faster than reported Magnevist renal clearance). Rapid kidney uptake could be improved by co-injection with diuretics, etc., which could enhance circulation time and increase tumor uptake. Hence, allowing for detection of smaller or flat lesions with greater sensitivity.
- Tumor bearing mice experienced uptake via gavage, indicated by bladder enhancement
  - Non tumor bearing mice for INAA had no measurable Gd in urine, indicating no uptake via gavage
  - While not wishing to be bound by theory, it is believed that uptake is by tumor-associated vasculature or other tumor related physiology
- While enhancement was observed in the bladder in the MM studies with the current compound, but was not observed in the previous study (16). And since Gd was not detected in the colon or urine by elemental analysis in the absence of a tumor. Again, while not wishing to be bound by theory, we hypothesize that the tumor uptake allowed systemic clearance and, hence, bladder contrast enhancement. But this would not be observed in normal, unaffected GI tracts that do not bear tumors.
- However, the tumor contrast enhancement by both the oral and intravenous routes of administration suggests that the current untargeted contrast agent could provide significant benefit when combined with standard MRI based virtual colonoscopy. The rapid systemic clearance of the agent through the renal system implies that intravenous administration has potential.
- Additionally, since this novel contrast agent has greater relaxivity than standard contrast, and rapid systemic clearance, also may demonstrate greater utility for contrast-enhanced MRI for a wide range of cancers in addition to colorectal cancers.
- It is also believed that the larger size, mass, of the current Gd-sucrose compound (3) could restrict extravasation in normal tissues, while allowing extravasation in tumors with more leaky vasculature, allowing for improved contrast with surrounding normal tissues.

Various changes may be made in the above disclosure without departing from the spirit and the scope of the disclosure. As another modification, a Gadolinium-DOTA sucrose-derived agent was synthesized using an argon-degassed solution of azide, octaalkyne in 9/1 THF/water, $CuSO_4$ and sodium ascorbate. The compound was improved by increasing the number of Gadolinium-DOTA chelates per sucrose to eight and shortening the chelates to induce stiffness and increase the rotational correlation time, inducing an eight-fold increase in Spin-Lattice-relaxivity. For in vivo assessment, SCID mice were intra-rectally injected with human CRC cells. Then, the mice received the Gadolinium-DOTA sucrose-derived agent (dissolved in sodium phosphate buffer at a concentration of 2.5 mM) by oral gavage, which increased tumor visualization by 40% above MRI with no contrast agent. Only mice with tumors (n=4) showed traces of the Gd-DOTA sucrose molecule in the bladder, compared to control mice (n=3) with no signal.

It is also to be understood that the following claims are intended to cover all of the generic and specific features of the disclosure herein.

REFERENCES

1. R. Siegel, C. DeSantis, K. Virgo, K. Stein, A. Mariotto, T. Smith, D. Cooper, T. Gansler, C. Lerro, S. Fedewa, C. Lin, C. Leach, R. S. Cannady, H. Cho, S. Scoppa, M. Hachey, R. Kirch, A. Jemal, E. Ward, Cancer treatment and survivorship statistics, 2012. *CA Cancer J Clin* 62, 220-241 (2012); published online Epub2012 July-August (10.3322/caac.21149).
2. O. Ben-Ishay, E. Brauner, Z. Peled, A. Othman, B. Person, Y. Kluger, Diagnosis of colon cancer differs in younger versus older patients despite similar complaints. *Isr Med Assoc J* 15, 284-287 (2013); published online EpubJun (
3. A. C. Society, "Cancer Facts & Figures, 2012," (American Cancer Society, 2012).
4. J. M. Walsh, J. P. Terdiman, Colorectal cancer screening: scientific review. *JAMA* 289, 1288-1296 (2003); published online EpubMar (
5. D. K. Rex, C. S. Cutler, G. T. Lemmel, E. Y. Rahmani, D. W. Clark, D. J. Helper, G. A. Lehman, D. G. Mark, Colonoscopic miss rates of adenomas determined by back-to-back colonoscopies. *Gastroenterology* 112, 24-28 (1997); published online EpubJan (
6. S. B. Ahn, D. S. Han, J. H. Bae, T. J. Byun, J. P. Kim, C. S. Eun, The Miss Rate for Colorectal Adenoma Determined by Quality-Adjusted, Back-to-Back Colonoscopies. *Gut Liver* 6, 64-70 (2012); published online EpubJan (10.5009/gnl.2012.6.1.64).
7. W. Luboldt, P. Bauerfeind, S. Wildermuth, B. Marincek, M. Fried, J. F. Debatin, Colonic masses: detection with MR colonography. *Radiology* 216, 383-388 (2000); published online EpubAug (
8. J. Yee, CT screening for colorectal cancer. *Radiographics* 22, 1525-1531 (2002); published online Epub2002 November-December (
9. P. J. Pickhardt, J. R. Choi, I. Hwang, J. A. Butler, M. L. Puckett, H. A. Hildebrandt, R. K. Wong, P. A. Nugent, P. A. Mysliwiec, W. R. Schindler, Computed tomographic virtual colonoscopy to screen for colorectal neoplasia in asymptomatic adults. *N Engl J Med* 349, 2191-2200 (2003); published online EpubDec (10.1056/NEJMoa031618).
10. B. Levin, D. A. Lieberman, B. McFarland, K. S. Andrews, D. Brooks, J. Bond, C. Dash, F. M. Giardiello, S. Glick, D. Johnson, C. D. Johnson, T. R. Levin, P. J. Pickhardt, D. K. Rex, R. A. Smith, A. Thorson, S. J. Winawer, A. C. S. C. C. A. Group, U. M.-S. T. Force, A. C. o. R. C. C. Committee, Screening and surveillance for the early detection of colorectal cancer and adenomatous polyps, 2008: a joint guideline from the American Cancer Society, the US Multi-Society Task Force on Colorectal Cancer, and the American College of Radiology. *Gastroenterology* 134, 1570-1595 (2008); published online EpubMay (10.1053/j.gastro.2008.02.002).
11. B. Saar, A. Meining, A. Beer, M. Settles, H. Helmberger, E. Frimberger, E. J. Rummeny, T. Misch, Prospective study on bright lumen magnetic resonance colonography in comparison with conventional colonoscopy. *Br J Radiol* 80, 235-241 (2007); published online EpubApr (10.1259/bjr/83959666).
12. G. Pappalardo, E. Polettini, F. M. Frattaroli, E. Casciani, C. D'Orta, M. D'Amato, G. F. Gualdi, Magnetic resonance colonography versus conventional colonoscopy for the detection of colonic endoluminal lesions. *Gastroenterology* 119, 300-304 (2000); published online EpubAug (
13. D. Hartmann, B. Bassler, D. Schilling, H. E. Adamek, R. Jakobs, B. Pfeifer, A. Eickhoff, C. Zindel, J. F. Riemann, G. Layer, Colorectal polyps: detection with dark-lumen MR colonography versus conventional colonoscopy. *Radiology* 238, 143-149 (2006); published online EpubJan (10.1148/radiol.2381041756).
14. W. Ajaj, G. Pelster, U. Treichel, F. M. Vogt, J. F. Debatin, S. G. Ruehm, T. C. Lauenstein, Dark lumen magnetic resonance colonography: comparison with conventional colonoscopy for the detection of colorectal pathology. *Gut* 52, 1738-1743 (2003); published online EpubDec
15. S. C. Goehde, E. Descher, A. Boekstegers, T. Lauenstein, C. Kühle, S. G. Ruehm, W. Ajaj, Dark lumen MR colonography based on fecal tagging for detection of colorectal masses: accuracy and patient acceptance. *Abdom Imaging* 30, 576-583 (2005); published online Epub2005 September-October (10.1007/s00261-004-0290-4).
16. G. V. Martinez, S. Navath, K. Sewda, V. Rao, P. Foroutan, R. Alleti, V. E. Moberg, A. M. Ahad, D. Coppola, M. C. Lloyd, R. J. Gillies, D. L. Morse, E. A. Mash, Demonstration of a sucrose-derived contrast agent for magnetic resonance imaging of the GI tract. *BioorgMed Chem Lett* 23, 2061-2064 (2013); published online EpubApr (10.1016/j.bmcl.2013.02.008).
17. P. Caravan, Protein-targeted gadolinium-based magnetic resonance imaging (MRI) contrast agents: design and mechanism of action. *Acc Chem Res* 42, 851-862 (2009); published online EpubJul (10.1021/ar800220p [pii] 10.1021/ar800220p).
18. V. Rao, R. Alleti, L. Xu, N. K. Tafreshi, D. L. Morse, R. J. Gillies, E. A. Mash, A sucrose-derived scaffold for multimerization of bioactive peptides. *BioorgMed Chem* 19, 6474-6482 (2011); published online EpubNov (10.1016/j.bmc.2011.08.053).
19. Martinez G V, Navath S, Sewda K, Rao V, Foroutan P, Alleti R, Moberg V E, Ahad A M, Coppola D, Lloyd M C, Gillies R J, Morse D L, Mash E A, "Demonstration of a sucrose-derived contrast agent for magnetic resonance imaging of the GI tract", Bioorganic & Medicinal Chemistry Letters 23 (2013) 2061-2064.

The invention claimed is:

1. A method of screening a patient for colon cancer using a computed tomographic (CT) or magnetic resonance (MR) colonography, said method comprising:
    dissolving a water soluble CT or MR contrast agent in an aqueous solution to produce an aqueous solution of colonography contrast agent;
    administering to a patient said aqueous solution of colonography contrast agent; and
    screening the patient for colon cancer using a computed tomographic colonography (CT-C) or a magnetic resonance colonography (MR-C), wherein the water soluble CT or MR contrast agent comprises a base or carrier scaffold formed of a polyhydroxol compound having a plurality of polyhydroxol functional groups, wherein each of said polyhydroxol functional group is linked to a moiety of the formula:

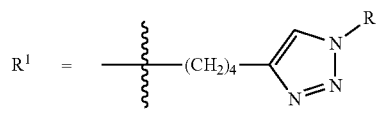

and wherein R comprises straight chain polyethylene glycol linker having on its terminal end a Gd-chelated DOTA moiety of the formula:

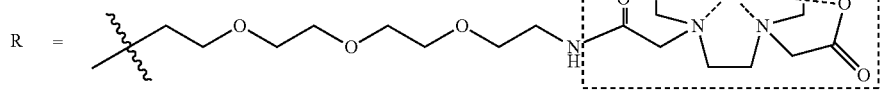

2. The method of claim 1, wherein the polyhydroxol compound comprises a disaccharide.

3. The method of claim 2, wherein the polyhydroxol compound comprises sucrose.

4. The method of claim 2, wherein the average number of Gd-DOTA chelates bonded to the sucrose is 8.

5. The method of claim 1, wherein the linker incorporates one or more straight chain hydrocarbon segments.

6. The method of claim 1, wherein the linker incorporates one or more branch chain hydrocarbon segments.

7. The method of claim 1, wherein colorectal cancer (CRC) cells are screened for.

8. The method of claim 1, wherein the molar relaxivity ($R_1$) of said water soluble CT or MR contrast agent is $213 \pm 1.7$ mM s$^{-1}$.

* * * * *